United States Patent [19]

Hardy et al.

[11] Patent Number: 4,864,866
[45] Date of Patent: Sep. 12, 1989

[54] MECHANICAL PROPERTY TESTING MACHINE

[76] Inventors: Raymond D. Hardy, P.O. Box 1574, Rowlett, Tex. 75088; Joe E. Greenslade, 2976 SE. Loop 820, Fort Worth, Tex. 76140

[21] Appl. No.: 180,349

[22] Filed: Apr. 11, 1988

[51] Int. Cl.[4] .............................................. G01N 3/30
[52] U.S. Cl. ........................................ 73/831; 73/834; 73/837; 73/845
[58] Field of Search ................. 73/834, 837, 825, 821, 73/840, 845, 791, 792, 793, 834

[56] References Cited

U.S. PATENT DOCUMENTS

| | | | |
|---|---|---|---|
| 1,445,963 | 2/1923 | LaBatt et al. | 73/825 |
| 3,142,980 | 8/1964 | Andersen | 73/834 |
| 3,203,232 | 8/1965 | Lehnig, Jr. | 73/796 |
| 3,559,472 | 2/1971 | Thompson, Jr. | 73/841 |
| 3,916,679 | 11/1975 | Voll et al. | 73/791 |
| 4,554,838 | 11/1985 | Paus | 73/834 X |

OTHER PUBLICATIONS

Kobayashi, H. et al., In Situ Tensile . . . Spectroscopy, Rev. Sci. Instrum. 51(5), May 1980, pp. 632–637.

*Primary Examiner*—Jerry W. Myracle
*Attorney, Agent, or Firm*—Henry W. Cummings

[57] ABSTRACT

In accordance with the present invention, a low in weight, portable, mechanical property testing machine is provided in which no special testing machine foundation is required, and a standard power supply may be used. The applied load to test the specimen is applied by the action of a rod making a single stroke within a cylinder containing hydraulic fluid. The inside diameter of the cylinder is significantly greater than the diameter of the rod. The hydraulic fluid transmitted from the cylinder is substantially ripple free and applies an even load to the specimen being tested through a second fluid cylinder and piston acting therein. The use of valves, as used in the prior art may thus be avoided, thus achieving simplicity of operation. To absorb the shock created by the specimen breaking, a dash pot is provided out board of the second piston as a shock absorber. When the specimen being tested is a threaded fastener, the fastener is gripped by a collet made of two threaded and tapered longitudinally split, pieces held together with a spring. As a load is applied to the specimen, the two collet pieces are locked together by the tapers, assuring thread alignment. The split collar also preferably has different threads per inch at each end of the collet pieces to adapt to different threads of different specimens. Split collars of different geometry are used to test thin, non-threaded specimens.

20 Claims, 4 Drawing Sheets

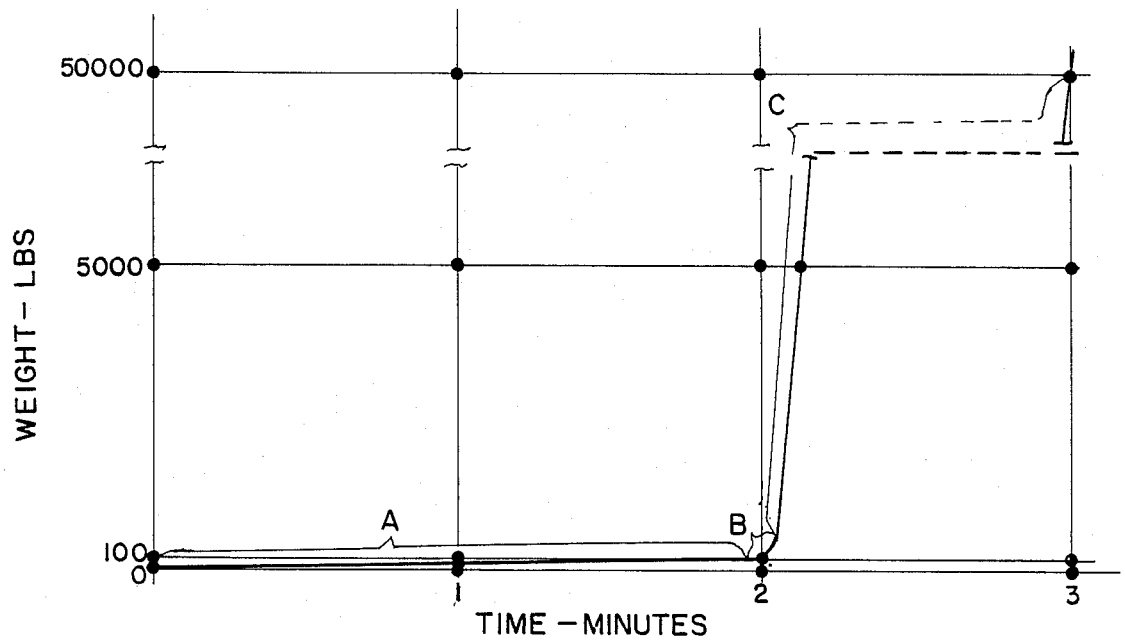
FIG. 6.
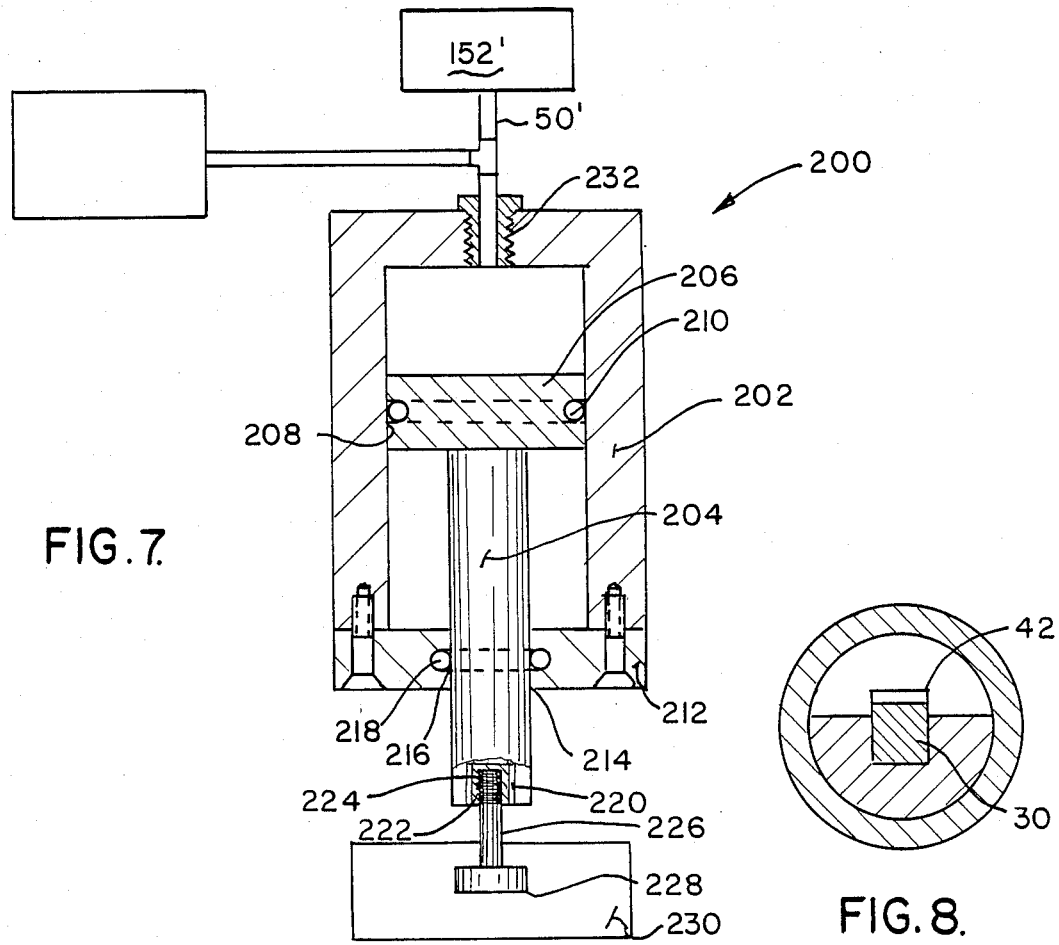
FIG. 7.
FIG. 8.

MECHANICAL PROPERTY TESTING MACHINE

BACKGROUND OF THE INVENTION

In U.S. Pat. No. 2,001,711 a portable tensile testing machine is disclosed which is operated through a fluid cylinder which is operated by a rack and pinion pump shown in FIG. 5, and a valve system shown in FIG. 6. The separate rod, the dash pot and the alignment collet does not appear to be shown.

U.S. Pat. No. 2,321,875 discloses the use of a single fluid cylinder in a tensile testing machine. The separate supply chamber, and rod operable therein, and dash pot, do not appear to be disclosed.

U.S. Pat. No. 3,329,010 discloses a tensile testing machine for fabrics. A fluid operating cylinder is used to apply the tensile force. The separate supply cylinder, the alignment collet, and the dash pot do not appear to be disclosed.

U.S Pat. No. 3,407,651 discloses a tensile testing machine in which the tensile load is applied at a high rate of speed by an explosive charge which severs a frangible member shown in FIG. 2. The collet alignment feature, and the single stroke of a hydraulic ram are not apparently disclosed. A dash shock absorber appears to be shown in FIG. 1 at 37.

U.S. Pat. No. 3,548,646 discloses a tensile testing assembly operated by high pressure gas applied to both sides of piston 15. The end of specimen 21 is located by co-operating tapers on the slot in piston 15, and an adjustable set screw. The single stroke hydraulic supply ram does not appear to be disclosed.

U.S. Pat. No. 3,934,464 discloses a pipe ring testing apparatus including a manually operated pump 40 and a tensile drive cylinder 16 controlled by valve 38. The specimens are semi-circular shoe discs. The rod-in-chamber, collet alignment feature, and the dash pot, do not appear to be shown.

SUMMARY OF THE INVENTION

A. Objects

One object of the present invention is to provide a testing machine which is light in weight and portable.

Another object of the invention is to provide a testing machine which can utilize a standard power supply.

Another object of the present invention is to provide a testing machine which is simple in operation.

Another object of the present invention is to provide a testing machine in which the machine is operated by a single stroke of a rod operating in a fluid cylinder.

Another object of the invention is to provide a testing machine in which alignment of the specimen in the machine is provided.

Another object of the invention is to provide a testing machine which uses a single adapter for both load and elongation testing.

Another object of the invention is to provide a collet design which is adaptable to different size threads.

Another object is to provide a cushion for any forces resulting from the specimen severing.

Another object is to provide a testing machine in which the applied load is continuously readable.

Another object of the invention is to provide a testing machine in which the entire stress strain curve may be determined and or/printed out.

Another object is to provide a testing machine in which tests cannot be made unless a protective cover is latched in place prior to the start of the test.

B. Summary

In accordance with the present invention, a low in weight, portable, mechanical property testing machine is provided in which no special testing machine foundation is required, and a standard power supply may be used. The applied load to test the specimen is applied by the action of a rod making a single stroke within a cylinder containing hydraulic fluid. The inside diameter of the cylinder is significantly greater than the diameter of the rod. The hydraulic fluid transmitted from the cylinder is substantially ripple free and applies an even load to the specimen being tested through a second fluid cylinder and piston acting therein. The use of valves, as used in the prior art may thus be avoided, thus achieving simplicity of operation. To absorb the shock created by the specimen breaking, a dash pot is provided out board of the second piston as a shock absorber. When the specimen being tested is a threaded fastener, the fastener is gripped by a collet made of two threaded and tapered longitudinally split, pieces held together with a spring. As a load is applied to the specimen, the two collet pieces are locked together by the tapers, assuring thread alignment. The split collar also preferably has different threads per inch at each end of the collet pieces to adapt to different threads of different specimens. Split collars of different geometry are used to test thin, non-threaded specimens. In a preferred embodiment, a reversible washer in which a first face is used to hold the fastener in place and in alignment in a first test, is also used to test the elongation of the fastener in a separate test, through the use of a second, tapered face. The load used in a given test is preferably continuously readable from a digital process controller which determines the applied load from the hydraulic pressure applied to the operating cylinder. The machine may also be used to determine the complete stress-strain curve for the specimen by computer print-out. The digital process controller will also store pertinent test information, and print out the information for review. As a safety feature, no tests can be run unless a safety cover is latched in place, which covers the testing apparatus. Specimens may be tested in tension, compression, and shear.

BRIEF DESCRIPTION OF THE DRAWINGS

FIG. 4b is an end view of FIG. 4a.

FIG. 6 is a graph of time against load resulting from the hydraulic supply unit.

FIG. 7 is a vertical sectional view of an embodiment of the invention directed to a compression testing machine.

FIG. 8 is a sectional view looking in the direction of the arrows along the line 8—8 in FIG. 1.

DESCRIPTION OF PREFERRED EMBODIMENTS

Figure 1:
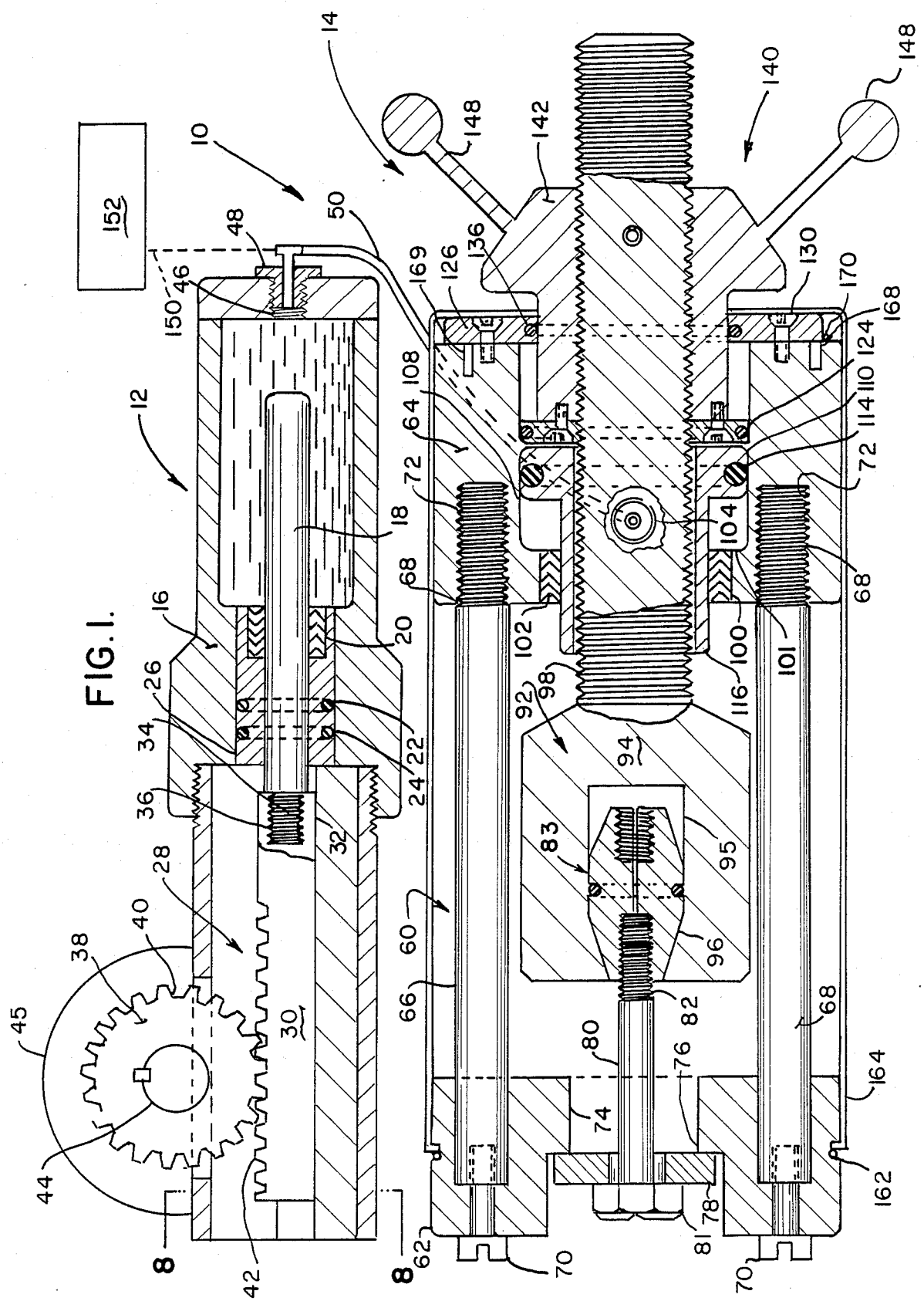
FIG. 1 is a schematic plan view of the mechanical property testing machine of the present invention.

The mechanical property testing machine of the present invention is indicated in the drawings at 10. The machine includes a hydraulic supply unit 12, and a testing unit 14 Preferably, both units are provided in a single contained housing which is light-weight, and portable, and which can readily be connected to existing power supplies, such as 110 Volt electricity, and/or conventional shop air pressure. No special testing machine foundation is required.

The supply unit includes a first fluid cylinder 16 having a rod 18 operable therein. The rod 18 extends through a packing 20, and a pair of "O" ring seals 22, and 24, which are located within a bore 26 in the cylinder 16. The rod 18 is of considerably smaller diameter than the inside diameter of cylinder 16.

The rod 18 is connected to a drive means 28. The drive means may comprise a rack and pinion, a nut and screw gear, an air cylinder, or another hydraulic cylinder. In the embodiment illustrated the drive means comprises a rack 30 connected at one end 32 to the outer end 34 of the piston 18 with a threaded fitting 36. The pinion 38 has teeth 40 which engage the teeth 42 on the rack 30.

The pinion 38 is mounted upon a rotatable shaft 44, driven by an appropriate power source, illustrated as an electric motor 45, an internal combustion engine, or another fluid cylinder. An important feature of the present invention is that it can be powered by readily available power sources, such as a 110, or 240 Volt electric motor, a conventional, low horse-power internal combustion engine, or conventional shop air.

FIG. 6 illustrates a plot of time of application of the rod into the cylinder 16 against resulting force which occurs from displacement of the rod within the cylinder. It is apparent that in portion A of the curve, the amount of load generated with time is relatively small. However, after the point B is reached a different rate of change of applied load with time occurs so that in the section C a great deal of applied load results from a small change in time. It is apparent that with the supply system of the present invention after the initial time period labeled A in FIG. 6 has transpired, a great deal of applied load results from a further movement of the piston as time progresses.

The cylinder 16 includes a threaded opening 46 which receives a threaded fitting 48 of a flexible hose 50. Flexible hose 50 carries hydraulic fluid from the cylinder 16 to the testing unit 14, and through a line 150 to a digital process controller 152.

Testing unit 14 includes a frame structure 60, including laterally spaced blocks 62, and 64. Elongated tie rods 66 extend between the blocks. Fasteners 70 hold the tie rods in place in block 62, and the ends 68 of the tie rods are threaded into threaded openings 72 in block 64.

Figure 2:
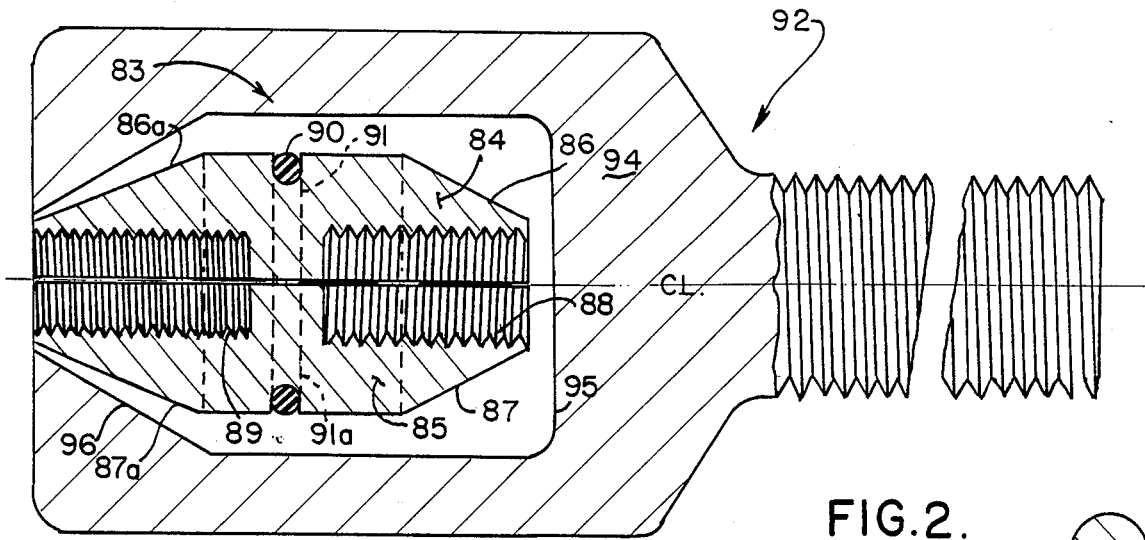
FIG. 2 is a detail view of the tension carrier illustrating the housing portion and the two piece collet.
Figure 3:
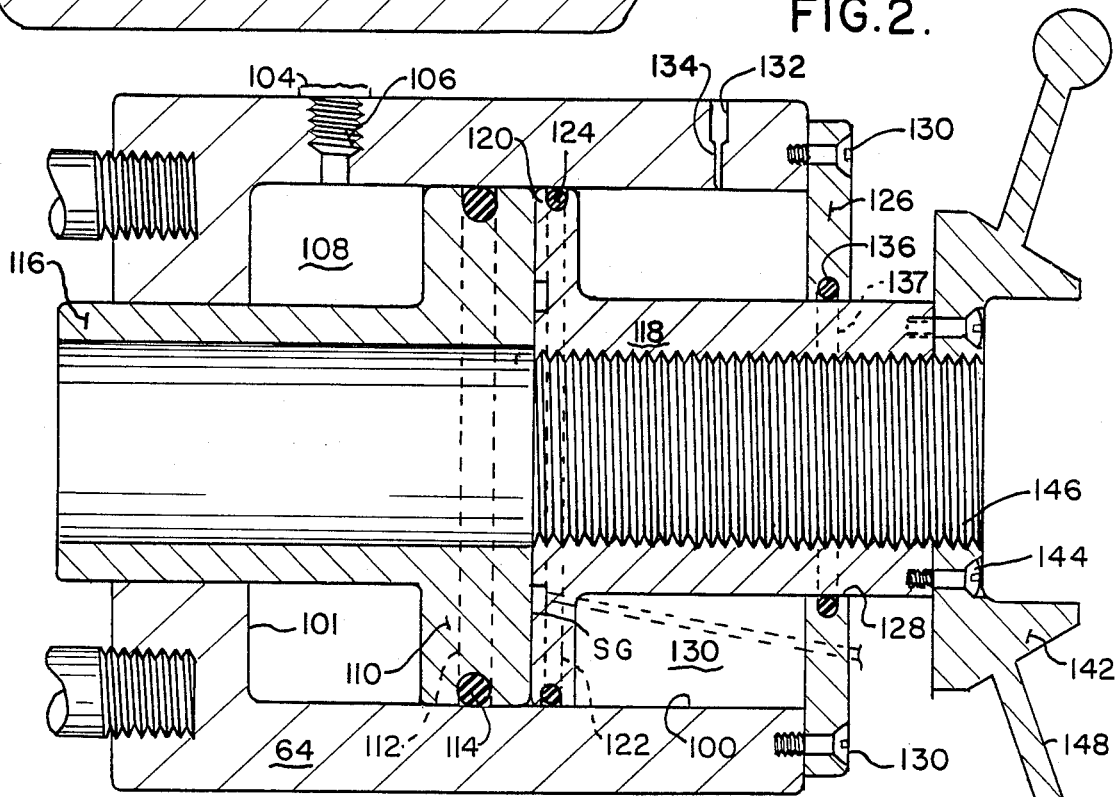
FIG. 3 is a detail view of the power cylinder, power piston, and dash pot used in the mechanical property testing machine of the present invention.
Figure 4:
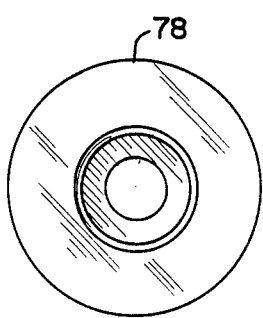
FIG. 4 is a view of the reversible washer of the present invention.
Figure 4A:
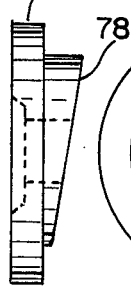
FIG. 4a is a side elevation view of FIG. 4.
Figure 4B:
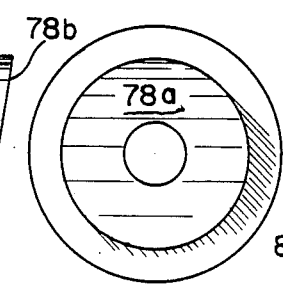
Figure 5:
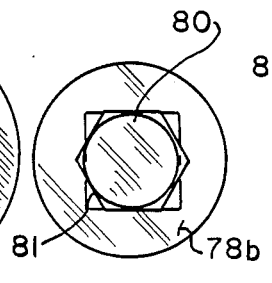
FIG. 5 is an end view of the use of the reversible washer.
Figure 5A:
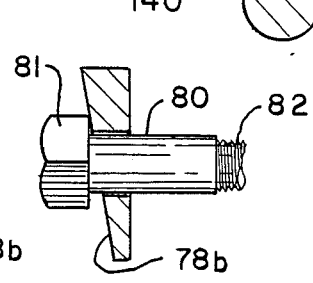
FIG. 5A is a view of the use of the tapered face of the reversible washer as used in the testing machine of the present invention.

Block 62 includes a bore 74 which defines a shoulder 76. A washer 78 of appropriate diameter is provided whereby a test specimen 80 having a head 81 will be held in place within block 62 of the testing unit 14. In a preferred embodiment of the invention the washer 78 is reversible, including a first face 78a shown in FIG. 4, for use in conventional direct alignment mechanical property testing, and a second face 78b for use in testing specimens requiring an elongation test according to ASTM Specification 5.52 (copy in application file). FIGS. 5 and 5A show the specimen mounted in place with tapered face 78b to make an elongation test in which the specimen rotates as the load is applied until the specimen severs. In either test, the specimen 80 is threaded at its inner end 82. The threaded inner end extends into a slot 95 in the body portion 94 of load carrier 92 (FIG. 2).

End 82 is threaded unto a two piece collet generally indicated at 83, including a pair of collet pieces 84 and 85. The pieces are cylindrical in shape and include respective outer tapered portions 86, 86a; and 87, 87a. The pieces are preferably threaded with different internal, standard threads at each end 88, and 89. The halves are essentially mirror images of each other, and are split along a longitudinal centerline, C.L. An "O" ring 90 is located in a slots 91, and 91a, respectively which extend around the two collet halves 84, and 85. The test specimen is threaded into both halves, according to the particular type of thread the specimen has and the "O" ring surrounds the halves and holds the assembly together when a test is to be made. The tapered collet edges 86, 86a; and 87, 87a; correspond to the taper 96 in the slot 95.

When a specimen is placed in the collet pieces and load carrier 92 in this manner, proper alignment for the test is assured. Furthermore, when the specimen breaks during the test, the portion of the broken fastener is readily removed because the collet pieces are longitudinally split.

Block 64 includes a bore 100 having a shoulder 101 into which extends a threaded extension 98 of load carrier 90. A packing 102 is provided in bore 100. A piston 110 includes a slot 112 to receive an "O" ring 114. Piston 110 includes a body portion 116 which is of larger diameter than load carrier extension 98. Hydraulic fluid supplied from the single stroke of rod 18 enters through fitting 104 and drives piston 110 from left to right in FIG. 1 to apply tension to specimen 80 through tension carrier 92.

The fitting 104 connected at the opposite end of flexible tube 50 extends into threaded port 106 to supply hydraulic fluid to second operating cylinder 108. Another flexible hose 150 extends to digital process controller 152.

Piston 110 essentially floats on load carrier extension 98 because of its greater diameter. A load carrier nut 118 is threaded unto load carrier extension 98, and includes a piston head 120 located adjacent piston head 110. Piston 110 is trapped between piston head 120, and the shoulder 101 in cylinder 64. A groove 122 in piston head 120 receives an "O" ring 124. A plate 126 having a round center opening 128 is held upon block 64 with fasteners 130 and defines with block 64 a dash pot chamber 131.

A vent opening 132 with a carefully sized cross section 134 is provided in block 64. Another "O" ring 136 is provided in a groove 137 in plate 126 to seal dash pot chamber 130.

After the fluid pressure applied into cylinder 108 causes piston 110 to move from left to right in FIG. 1, with sufficient force to break specimen 80, the dash pot chamber 130 cushions movement of tension carrier 90 as air exits vent 132 and small cross section 134.

A handle 140 including a body portion or hub 142 is attached to carrier nut 118 with fasteners 144, and is threaded at 146 to engage load carrier extension 98. The arms 148 extending radially outwardly from the body portion or hub 142 facilitate locating load carrier nut 118, piston 120, and piston 110 in the proper location within block 64. Since piston 110 is movable with respect to load carrier extension 98, this allows different length fasteners to be tested, and also locates piston 110 within block 64.

Digital process controller 152 is a commercially available load reading device which is computer controlled. The applied load is continuous readable from the unit. The unit also stores mechanical property data such as tensile strength, compressive strength, elongation, and reduction in area. One or more of these parameters can be continuous, read and/or plotted by the controller. The entire stress strain curve may be plotted for a test if desired. As an example an Eaton Quality Signature Q5-200 may be used. Additional information may be obtained from Eaton Corp; Automation Products Div.; 901 S. 12th St., Watertown, WI; 53094. The applied load, and the stress-strain data may also be obtained with a strain gauge S.G. in FIG. 2 supplying the data through leads shown dotted. Cover 160 is pivotable mounted on unit 14, on block 14 at 162. The cover includes a body portion 164 and a distal end 166 having a catch 168 which engages a latch 169. Latch 169 controls an electrical switch 170. Switch 170 controls the electrical circuit to motor 45 and computer controller 152. These units will not be connected if cover 160 is not latched in place.

In operation, to test a specimen, a washer 78 of the proper diameter with face 78a is selected to hold specimen head 81 in place. Handle 140 is used to move piston 110 and load carrier nut 130 to the proper location for this specimen in cylinder 108. The threaded end 82 of specimen is then threaded into both pieces 84 and 85 of the collet 83, with the hollow ring 90 located around the collet pieces. With cover 160 closed electric motor 45 is used to rotate shaft 44 and pinion 38. This moves rack 30 and rod 18 from left to right in FIG. 1, and in a single stroke forces sufficient hydraulic fluid from cylinder 16 through fitting 48 and flexible tube 50 into chamber 108 to move piston 110 from left to right in FIG. 1, to first move tapers 86a and 87a into engagement with load carrier taper 96 to achieve proper specimen alignment. This applies sufficient tensile force to sever specimen 80. When the specimen is severed the force is applied into dash pot 130 by load carrier nut piston 120, causing air to exit slowly through controlled vent section 134. This cushions the load carrier assembly. The severed specimen is easily removed with head 81 and collet portions 83 and 84. The stress-strain curve and other relevant data from process controller 152 may be printed out. If desired, an elongation test may then be made with the adapter face 78b holding the specimen in place as shown in FIG. 5A, and additional test data and specimen severing strength under this load condition obtained.

As mentioned above, a strain gauge S.G. in FIG. 2 located in a groove in piston 120, having electrical leads shown dotted in FIG. 2 may also be used to supply the data to the process controller 152. A different process controller than the specific one mentioned above should be used which reads electrical stress-strain data instead of one that reads pressure.

Another embodiment of the present invention is shown in FIG. 7. In this embodiment a compression testing machine 200 includes a cylinder 202 having a piston 204 movable back and forth therein which has a piston head 206 and a groove 208 which receives an "O" ring seal 210. Cylinder 202 includes a transverse member 212 having an opening 214 and a groove 216 which receives an "O" ring 218 which seals piston 204.

Piston 204 includes an opening 220 which receives a threaded collet 222 which receives a threaded end 224 of a compression test specimen 226. The opposite end of specimen 226 is held in place upon a compression test mounting block 230. A flexible conduit 50' carrying hydraulic fluid from cylinder 16 is connected to a fitting 232.

In operation, a single stroke of rod 18 in cylinder 16 causes hydraulic fluid to enter cylinder 202 and move piston 204 such as to apply a compressive load to specimen 220. The applied load and other parameters may be read out by digital process controller 152, including compressive strength elongation in compression, etc.

It is apparent from FIG. 7 that the supply cylinder 16 and rod 18 may be used to supply an applied load to a compression test as well as a tensile test.

The supply cylinder 16, and rod 18 may also supply an applied load to a shear test by pulling or pushing one portion of a shear test specimen, with respect to another portion of the specimen. This is described in greater detail in connection with FIG. 11, hereinafter.

Figure 9:
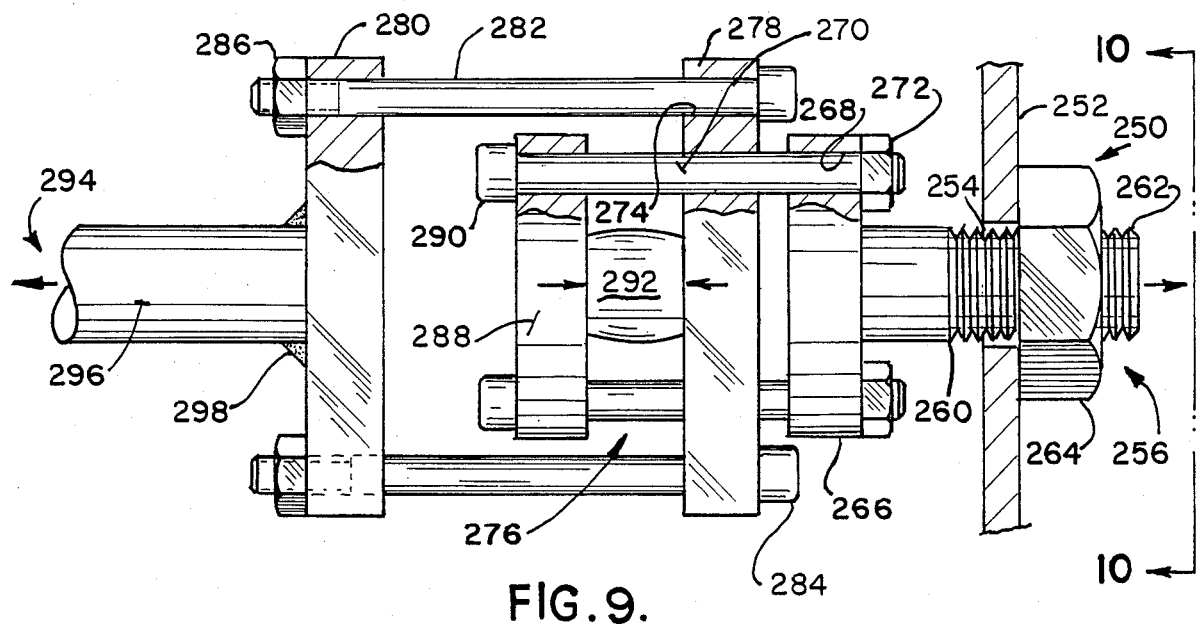
FIG. 9 is a sectional view of another compression testing embodiment of the present invention.
Figure 10:
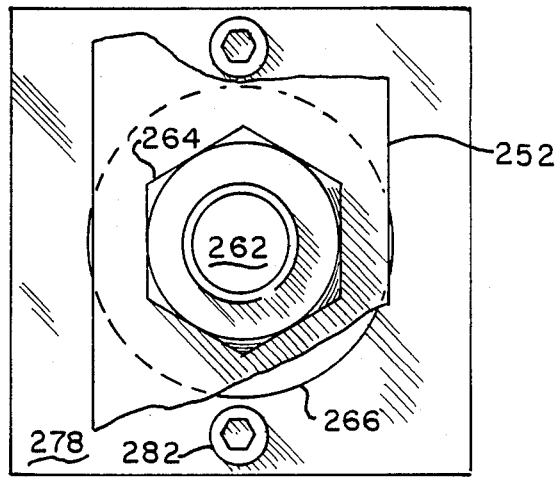
FIG. 10 is an end view of FIG. 9.

Another embodiment of the invention is shown in FIGS. 9 and 10. In this embodiment another compression testing unit 250 includes a test frame 252 having an opening 254 which receives a stationary compression fixture 256 including a bolt 260 having a threaded end 262 held place with a nut 264. Fixture 256 further includes a plate 266 with openings 268 which receive tie rods 270 held in place with fastener nuts 272.

Rods 270 extend through openings 274 in a movable compression fixture 276 including plates 278 and 280 and tie rods 282 extending therebetween held in place, respectively with fasteners 284 and 286. Rods 270 extend to a plate 288 inside movable fixture 276, and are held in place with fasteners 290. A specimen 292 for testing is located between plates 278 and 288.

A load carrier 294 includes a shaft portion 296 which extends up to plate 280 and is welded thereto with a weld 298.

In operation, specimen 292 is tested in compression by a compressive load applied to load carrier 294 by a suitable means such as movement of hydraulic fluid form cylinder 16 by the action of rod 18 into cylinder 108. Movable fixture 276 moves from right to left in FIG. 9 until sufficient compressive load is applied to specimen 292 to sever the same in compression. Preferably the applied load is read out on digital process controller 152, and the resulting load is cushioned by dash pot 130.

Figure 11:
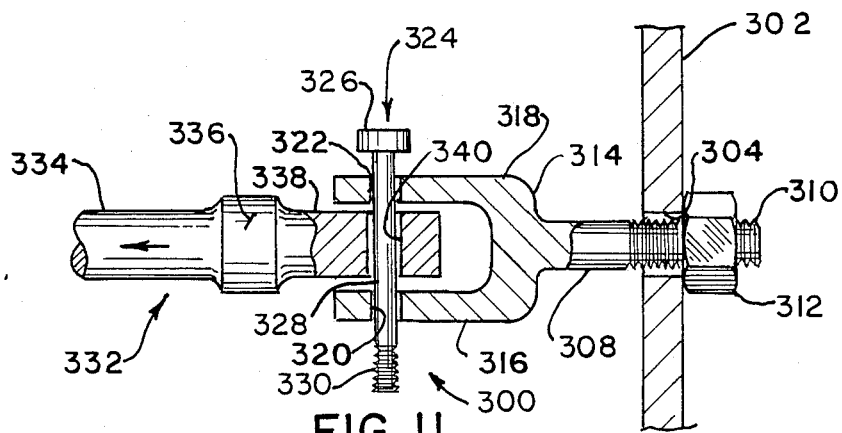
FIG. 11 is a sectional view of a shear test embodiment of the present invention.

Another embodiment of the invention is shown in FIG. 11. In this embodiment a shear test fixture is shown at 300. In this embodiment, a fixture frame 302 includes an opening 304 which receives a stationary shear fixture 306. Stationary fixture 306 includes a bifurcated rod 308 which is threaded at its outer end 310 and receives a nut 312 to hold it in place within the frame 302.

Bifurcated rod 308 includes a body portion 314, and legs 316 and 318 which have respective openings 320, and 322, which receive a shear specimen 324 having a head 326, a shank portion 328, and a threaded distal end 330. A load carrier 332 including a body portion 334, a head 336, and a specimen engaging portion 338, and a specimen receiving opening 340 is provided.

In operation, with a specimen 324 in place as shown in FIG. 11, a suitable force, such as hydraulic fluid from cylinder 16 actuated by rod 18 transferred into to cylinder 108 causes load carrier 332 to move from right to left in FIG. 11, which applies a shear load to specimen 324. The applied shear load may be read out on digital process controller 152. When the specimen shears, if the load is applied with enough force to sever the specimen, the resulting severing load is preferably cushioned by dash pot 130.

It is thus apparent that the mechanical property testing machine of the present invention may be used to test specimens loaded in tension, compression, and shear.

What is claimed is:

1. An improved mechanical property testing machine comprising:
   means for supporting a specimen to be tested;
   carrying means for applying a test load including a specimen testing cylinder, and a test piston moveable therein to apply a test load to the specimen;
   a supply hydraulic cylinder;
   a rod moveable therein having an outside diameter significantly less than said supply cylinder;
   power means for applying a force to said rod of sufficient force whereby with a single stroke of said rod, hydraulic fluid is conveyed to said test cylinder whereby a test load is applied to said specimen;
   means for obtaining alignment between said specimen and said carrier comprising a multi-piece collet which is split longitudinally which threadably engages said pieces; and
   a resilient member surrounding said collet pieces to hold the assembly together.

2. An improved testing machine according to claim 1 wherein the cushioning means comprises a dash pot located outboard of said test piston.

3. An improved testing machine according to claim 1 wherein the specimen and collet pieces are received within a tapered opening in said carrier and wherein the collet pieces include tapers which engage the taper on said carrier, and wherein said collet pieces are threaded with different threads at each end.

4. An improved mechanical property testing machine comprising:
   means for supporting a specimen to be tested;
   carrying means for applying a test load including a specimen testing cylinder, and a test piston movable therein to apply a test load to the specimen;
   means for obtaining alignment between said specimen and said carrying means;
   a supply hydraulic cylinder;
   a rod movable therein having an outside diameter significantly less than said supply cylinder;
   means for applying a force to said rod of sufficient force whereby with a single stroke of said rod, hydraulic fluid is conveyed to said test cylinder, whereby a test load is applied to said specimen; conduit means for supplying sufficient hydraulic fluid to said cylinder to sever said specimen;
   means for cushioning the force resulting from severing the specimen comprising a dash pot located outboard of said test piston; and
   wherein said test cylinder and said dash pot are located adjacent each other.

5. An improved testing machine according to claim 4 wherein said rod is driven by a rack attached to the outer end of said supply piston, and a pinion which engages said rack.

6. An improved mechanical property testing machine according to claim 4 wherein the machine is connected to a digital process controller which continuously reads a desired parameter and stores data for calculating other parameters.

7. An improved mechanical property testing machine according to claim 6 wherein an applied load is printed out by the digital process controller.

8. An improved mechanical property testing machine according to claim 7 wherein a stress strain curve is plotted out by the digital process controller.

9. An improved mechanical property testing machine according to claim 4 wherein the mechanical property tested is a tensile load and wherein the properties measured are tensile properties.

10. An improved mechanical property testing machine according to claim 4 wherein the test load is applied to compress a specimen and wherein compressive mechanical properties are measured.

11. An improved mechanical property testing machine according to claim 4 wherein the applied load is applied to shear a specimen, and shear mechanical properties are measured.

12. An improved load testing machine comprising:
   means for locating a specimen to be tested in said machine;
   a power cylinder for receiving hydraulic fluid and a power piston to apply a testing load to said specimen;
   means for applying hydraulic fluid to said power cylinder to displace said piston;
   a dash pot located outboard of said power piston to cushion any forces resulting from severing said specimen; and
   wherein the piston head for the test cylinder is located adjacent the piston head for the dash pot.

13. An improved load testing machine comprising:
   means for locating a specimen to be tested in said machine;
   a test cylinder for receiving hydraulic fluid and a test piston to apply a tensile load to said specimen;
   means for applying hydraulic fluid to said test cylinder to displace said test piston;
   a dash pot located outboard of said test piston to cushion any forces resulting from severing said specimen; wherein the piston head for the test cylinder is located adjacent the piston head for the dash pot, and is movable back and forth by said dash pot piston.

14. An improved mechanical property testing machine comprising:
   means for supporting a specimen to be tested;
   carrying means for applying a test load including a specimen testing cylinder, and a test piston movable therein to apply a test load to the specimen;
   a supply hydraulic cylinder;
   a rod movable therein having an outside diameter significantly less than said supply cylinder;

means for applying a force to said rod of sufficient force whereby with a single stroke of said rod hydraulic fluid is conveyed to said test cylinder whereby a test load is applied to said specimen; and including safety means to prevent operating of the machine unless the safety means are in the safe operation position.

15. An improved mechanical property testing machine comprising:
means for supporting a specimen to be tested;
carrying means for applying a test load including a specimen testing cylinder, and a test piston movable therein to apply a test load to the specimen;
means for obtaining alignment between said specimen and said carrying means;
a supply hydraulic cylinder;
a rod movable therein having an outside diameter significantly less than said supply cylinder;
means for applying a force to said rod of sufficient force whereby with a single stroke of said rod, hydraulic fluid is conveyed to said test cylinder, whereby a test load is applied to said specimen; conduit means for supplying sufficient hydraulic fluid to said cylinder to sever said specimen;
means for cushioning the force resulting from severing the specimen comprising a dash pot located outboard of said test piston; said test cylinder and said dash pot located adjacent each other; and
said carrier including a threaded extension, and wherein said specimen is held in place with a reversible adapter for mechanical property testing.

16. An improved load testing machine comprising:
means for locating a specimen to be tested in said machine; a power cylinder for receiving hydraulic fluid and a power piston to apply a testing load to said specimen;
means for applying hydraulic fluid to said power cylinder to displace said piston;
a dash pot located outboard of said power piston to cushion any forces resulting from severing said specimen; the piston head for the power cylinder being located adjacent the piston head for the dash pot; and wherein the weight of the machine does not exceed about 300 pounds, and is therefore portable.

17. An improved mechanical property testing machine according to claim 16 wherein the machine is operable by readily available standard power source.

18. An improved mechanical property testing machine according to claim 17 wherein the readily available power source is 110 volt electricity.

19. An improved mechanical property testing machine according to claim 17 wherein the readily available power source is ordinary shop air.

20. An improved mechanical property testing machine comprising:
means for supporting a specimen to be tested; carrying means for applying a test load including a specimen testing cylinder, and a test piston movable therein to apply a test load to the specimen;
a supply hydraulic cylinder;
a rod movable therein having an outside diameter significantly less than said supply cylinder;
means for applying a force to said rod of sufficient force whereby with a single stroke of said rod hydraulic fluid is conveyed to said test cylinder whereby a test load is applied to said specimen;
including safety means to prevent operating of the machine unless the safety means are in the safe operation position; and
wherein safety means include an electrical switch which prevents operation of the machine unless the machine is in the safe position.

* * * * *